US009442936B2

(12) United States Patent
Zhang et al.

(10) Patent No.: US 9,442,936 B2
(45) Date of Patent: *Sep. 13, 2016

(54) COOPERATIVE GRID BASED PICTURE ARCHIVING AND COMMUNICATION SYSTEM

(71) Applicant: Axon Medical Technologies Corp., Toronto (CA)

(72) Inventors: Jianguo Zhang, Shanghai (CN); Yuanyuan Yang, Shanghai (CN); Jin Jin, Shanghai (CN); Jianyong Sun, Shanghai (CN)

(73) Assignee: Axon Medical Technologies Corp., Toronto (CA)

( * ) Notice: Subject to any disclaimer, the term of this patent is extended or adjusted under 35 U.S.C. 154(b) by 91 days.

This patent is subject to a terminal disclaimer.

(21) Appl. No.: 14/299,812

(22) Filed: Jun. 9, 2014

(65) Prior Publication Data

US 2014/0289206 A1 Sep. 25, 2014

Related U.S. Application Data

(63) Continuation of application No. 12/521,199, filed as application No. PCT/CA2007/001972 on Nov. 2, 2007, now Pat. No. 8,805,890.

(30) Foreign Application Priority Data

Dec. 27, 2006 (CN) .......................... 2006 1 0148064

(51) Int. Cl.
*G06F 17/24* (2006.01)
*G06F 17/30* (2006.01)
*G06F 19/00* (2011.01)

(52) U.S. Cl.
CPC ..... *G06F 17/30073* (2013.01); *G06F 17/3028* (2013.01); *G06F 19/321* (2013.01)

(58) Field of Classification Search
CPC ........... G06F 19/321; G06F 17/30073; G06F 17/3028
See application file for complete search history.

(56) References Cited

U.S. PATENT DOCUMENTS 5,671,353 A * 9/1997 Tian ...................... G06F 19/321
714/37
7,054,955 B2 5/2006 Chen et al.
(Continued)

FOREIGN PATENT DOCUMENTS

CN 1996847 A 7/2007
WO 2008077232 A1 7/2008

OTHER PUBLICATIONS

Foreign communication from a priority application—International Search Report and Written Opinion, PCT/CA2007/001972, Feb. 18, 2008, 9 pages.

(Continued)

*Primary Examiner* — Tarek Chbouki
(74) *Attorney, Agent, or Firm* — Conley Rose, P.C.; Rodney B. Carroll (57) ABSTRACT

A Cooperative Grid Based Picture Archiving and Communication System (Grid PACS for short) is a multimedia (imaging) medical information archiving, communication and application system used in hospitals. Based on the existing PACS servers, workstations, or other networked multimedia image management systems, it adds and integrates grid-based network functionality into the existing image systems to form new grid-based image communication and management system.

It uses service-oriented and event-driven concepts and methods to design and implement a new grid-based image communication and management system to solve the problems encountered in distributing archived image information, coordinating work and managing in a virtually centralized way (Virtual Super-PACS) of different PACS or archiving systems under varied operating environments.

11 Claims, 8 Drawing Sheets

(56) References Cited

U.S. PATENT DOCUMENTS

| | | | |
|---|---|---|---|
| 7,249,281 B2 | 7/2007 | Shirley et al. | |
| 7,623,696 B2 | 11/2009 | Deaven et al. | |
| 7,716,180 B2 | 5/2010 | Vermeulen et al. | |
| 7,805,407 B1 | 9/2010 | Verbeke et al. | |
| 7,813,594 B2 | 10/2010 | Edwards et al. | |
| 7,822,711 B1 | 10/2010 | Ranade | |
| 8,015,032 B2 | 9/2011 | Keen | |
| 8,131,562 B2 | 3/2012 | Hernandez et al. | |
| 8,225,215 B2 | 7/2012 | Oswalt | |
| 8,805,890 B2 | 8/2014 | Zhang et al. | |
| 2002/0172498 A1 | 11/2002 | Esenyan et al. | |
| 2003/0187689 A1* | 10/2003 | Barnes | G06Q 50/22 705/2 |
| 2003/0204420 A1 | 10/2003 | Wilkes et al. | |
| 2004/0034550 A1* | 2/2004 | Menschik | G06F 19/322 705/3 |
| 2004/0061889 A1 | 4/2004 | Wood et al. | |
| 2005/0021512 A1 | 1/2005 | Koenig | |
| 2006/0085696 A1* | 4/2006 | Bauer | G06F 11/3006 714/47.1 |
| 2006/0106877 A1 | 5/2006 | Lee | |
| 2006/0122482 A1 | 6/2006 | Mariotti et al. | |
| 2006/0143046 A1 | 6/2006 | Kawakami et al. | |
| 2006/0167945 A1 | 7/2006 | Trautner | |
| 2006/0182324 A1 | 8/2006 | Motoki | |
| 2006/0293917 A1* | 12/2006 | Bao | G06F 19/321 705/2 |
| 2007/0061393 A1 | 3/2007 | Moore | |
| 2007/0107033 A1* | 5/2007 | Ho | G06F 11/1451 725/115 |
| 2007/0197909 A1 | 8/2007 | Kariathungal et al. | |
| 2007/0237402 A1 | 10/2007 | Dekel et al. | |
| 2007/0270695 A1* | 11/2007 | Keen | G06F 19/321 600/448 |

OTHER PUBLICATIONS

Foreign communication from a priority application—International Preliminary Report on Patentability, PCT/CA2007/001972, Jun. 30, 2009, 6 pages.

* cited by examiner

Figure 12

COOPERATIVE GRID BASED PICTURE ARCHIVING AND COMMUNICATION SYSTEM

CROSS-REFERENCE TO RELATED APPLICATIONS

This application is a continuation of and claims priority to U.S. patent application Ser. No. 12/521,199 filed on Mar. 9, 2010, published as US 2010/0235323A1 and entitled "Cooperative Grid Based Picture Archiving and Communication System," which is a filing under 35 U.S.C. 371 of International Application No. PCT/CA2007/001972 filed Nov. 2, 2007, entitled "Cooperative Grid Based Picture Archiving and Communication System," claiming priority of Chinese Patent Application No. CN 200610148064.1 filed Dec. 27, 2006, which applications are incorporated by reference herein in their entirety.

FIELD OF INVENTION

The invention is in the domain of information communication, computer and medical technology. It deals especially with hospital's existing medical picture archiving and communication system (PACS for short), Radiological Information System (RIS for short), Electronic Patient Record system (EPR for short), Hospital Information Management System (HIS for short).

BACKGROUND OF THE INVENTION

With the digitization of various medical information as well as the wide use of world wide web and its related technologies, research has quickened its pace in utilizing high speed information networks to build wide area Electronic Patient Record system EPR for short) after having progressively perfected the construction of hospital information digitization. It is achieved mainly by connecting a patient's information stored in various hospitals through a high speed network (Internet or private network), making it easy to mutually transfer the patient's health record, including diagnostic reports, clinical records, radiological images, laboratory testing information and so on, according to the patient's medical conditions and needs, in the network among hospital's various internal departments, various hospital information systems as well as various hospitals. There is a need for hospitals' various medical information systems (PACS, RIS, HIS, EPR etc.,) be integrated and that seamless flow of multimedia data be realized between the information systems, so that a clinician may effectively use medical information, improve clinical diagnosis, the level of treatment, healthcare service, service quality and efficiency, and meanwhile, greatly save on resources.

The main bottleneck in integrating various kinds of hospital imaging information systems such as cross-vendors PACSs to achieve seamless medical data flow between them is: various systems are developed by different companies while radiological medical images are mostly high definition (≥2Kx2K, such as CR, DR, Mammography etc), big file sizes (60-400 Megabytes, such as MR, CT, US Series etc.,), and appear in various network archiving situations, various media forms (static images, dynamic images, two-dimensional or three-dimensional and so on). Under the precondition of ensuring medical diagnosis quality, it is very difficult to perfectly realize safe, reliable, efficient and high speed data archiving and retrieval. Although there were some systematic solutions before this, there is still not one system able to integrate the distributed, differently structured archived resources including DICOM images, non-DICOM images, text, audio and such multimedia resources and centering around the patient, centrally manage the resources in a virtual way and safely and reliably operate without interruption.

SUMMARY OF THE INVENTION

The invention aims to solve the following technical problems: how to overcome insufficiencies of existing image communication and management technologies, how to take advantage of the network to build virtual central networked image management environment and how to produce a design which fully utilizes various archived resources on the basis of various existing developed PACS systems and transform them into an easily accessible, reliable, standard as well as economical archiving system. This invention's objective is to provide a virtual central picture archiving and multimedia communication system based on a cooperative grid concept and to provide its realization method. Its characteristics are that it utilizes service-oriented and event-driven methods, and grid concept to realize distributed archiving, disaster recovery backup, optimized multi-thread retrieval, virtual centralized management in various PACS of various conditions or of various types. It also makes these PACS or picture archiving systems to work cooperatively, thus achieving a safe and reliable Virtual Super PACS system.

TECHNICAL DESIGN OF THE INVENTION

The invention proposes a Cooperative Grid Based Picture Archiving and Communication System (Grid PACS for short). It may include many PACS Agent Nodes containing PACS server module bases (including basic DICOM image communication services and database management functionality), a connected Master Node and various Client Ends, forming a PACS Agent Node<-> Master Node<-> Client End three level working structure. Additionally, it may also use PACS Agent Node<-> Master Node as a First Grid Agent Node to connect again with another Master Node and various Client End to form a new three level structure, in which a two level structure formed by a PACS Agent Node and another Master Node may act as Grid Middleware to communicate with third-party PACS (or imaging equipment) through DICOM (or other types of communication based on TCP/IP protocol).

The PACS Agent Node, besides the original PACS function, also include the functions of: uploading received image index information, collecting local resource monitor and control information, deleting images regularly online or offline images; receiving automatic routing or backup communication messages from Master Node and manipulating images according to compression or backup commands or messages from Master Node; querying the Master Node through the Web services provided by the Master Node after receiving the query requests (e.g., DICOM C-Find Request) from the third part PACS components, and sending the query results back (e.g., DICOM C-Find Responds)to the third PACS components, then retrieving images from other PACS Agent nodes, the operation of which are directed by the Master Node, through FTP, http or other kinds of image communication protocols after receiving image retrieval request (e.g., DICOM C-Move Request) from the third part PACS components or through other PACS Agent Nodes to get images from other PACS components.

The Master Node include multiple database function modules, grid messages processing logic modules and grid message communication and processing service modules, in which the database of the Master Node is a two levels structure. It includes upper level sharing database, and lower level database modules which consists of Local DB module and Same Level Resources DB module. The Local DB module includes Task Management DB module, Image Resources DB module and Other Resource DB module. The index information such as UIDs, patient names of the shared images or other types of patient medical records to outside of the PACS Grid are managed by upper level database, and these index information come from the lower level database of Local DB module and Same Level Resources DB module. The information of Image Resources DB and Other Resource DB modules in the Local DB module of a Master Node can be duplicated to the Same Level Resource DB modules of all other Master Nodes through the database synchronization mechanism or other kinds of data duplication methods with synchronously or asynchronously at regular intervals. This kind of duplication make all of Master Nodes in a Grid PACS be identical for all of End Clients of the Grid querying the patient images or other medical records stored or managed by the Grid PACS.

Figure 2:
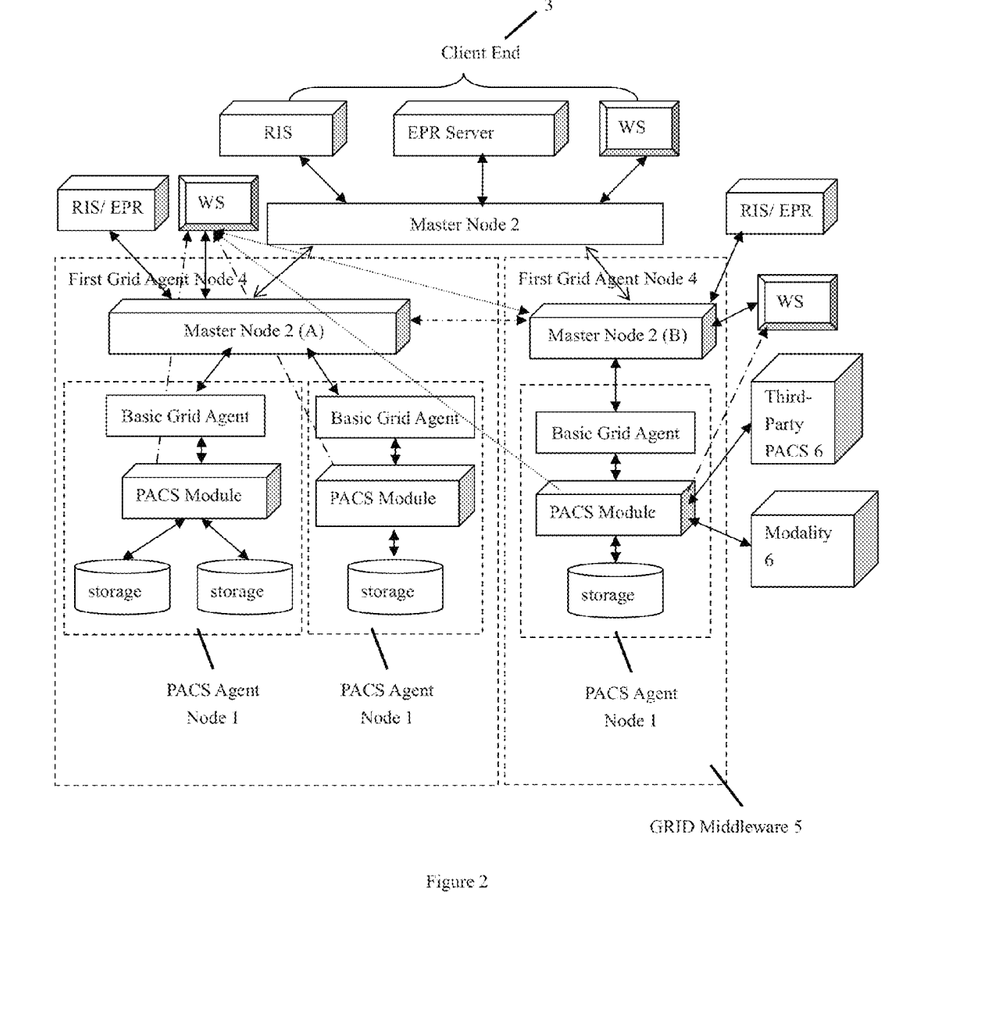
FIG. 2 is the structural illustration of a case of implementation of the invention's Cooperative Grid Based Picture Archiving and Communication System.

The functions of the Master Node Grid Processing Logic module include: providing query services of the registration information of patients' images or other resource to outside, synchronizing the registration information with directly attached PACS Agent Nodes and other Same Level Master Nodes if there are many Master Nodes in the Grid, allocating automatic backup commander messages to specific indicated PACS Agent Nodes, processing events or messages received from PACS Agent Nodes or Client Ends, sending disaster recovery commands to PACS Agent Nodes, and managing its connected PACS Agent Nodes and Client Ends, as well as any Master Node and Client Ends under the hierarchically connected environment as showed in FIG. 2.

The service modules of Master Node provides various kinds of services to the Client Ends, PACS Agent Nodes, and Same Level Master Nodes, which include validation of resources, registration services, synchronization service, deletion services, query services, message services, monitoring and control services.

The various Client Ends include RIS servers, EPR servers and PACS display workstations, as well as some of PACS Agent Nodes. RIS servers or EPR servers may be installed with modules for receiving and validating registration information as well as the query module. The PACS display workstation may be installed with query module. PACS Agent Nodes may be installed the protocol converting modules which can convert DICOM (or other kinds of communication protocols) Query request/respond commands from/to a PACS component to Web-based query request/respond to/from Master Node, and DICOM Retrieval request (C-Move) commands from/to a PACS component to image retrieval request/respond communication protocols (such as FTP, http) to/from other PACS Agent Nodes under directing of Master Node.

In the PACS Agent Node<-> Master Node<-> Client End three level working structure, information such as external and internal grid messages or events transfer between them may be realized by means of Web Service(or other types of communication based on TCP/IP) provided by the various levels. The system may be configured for various operation system platforms (Microsoft Windows or UNIX/LINUX).

The Grid Middleware actively queries and retrieves or passively receives third party PACS(or imaging equipment, such as CT/MR/Digital X-Ray/Ultra-sound etc.) images, or multimedia medical information through DICOM Query/Retrieve C-Find/C-Move and C-Store SCP (or other types of communication protocols based on TCP/IP), transfers Client End's image information retrieval request to third party PACS system by means of DICOM C-Move or WADO(or other communication protocols), and through PACS Agent Node, sends the images archived by a third party PACS to a Client End.

The Specific Workflow is:

(1) Archived Image or Multimedia Medical Information Resources Registration Workflow After receiving new images, the PACS server module in PACS Agent Node puts images or series of images as jobs into a queue according to basic image series information. The PACS Agent Node then gets the image or series jobs from the queue, parses the content of images, get UIDs of the patient, study, series and images, creates XML-based manifest containing the UIDs of the patient, study, series and images named as the registration information, and upload the manifest to the Master Node by using the registration service provided by Master Node.

The PACS Agent Node may actively query third party PACS component (DICOM Server, or Workstation) by using DICOM C-Find SCU or third party PACS communication APIs to get UIDs of a specific patient, study, series and images, creates XML-based manifest containing the UIDs of the patient, study, series and images named as the registration information, and upload the manifest to the Master Node by using the registration service provided by Master Node.

The Master Node registration service receives and decodes the manifest to get UIDs of the patient, study, series and images, and then stores the registration information into the local Image Resources DB module; and may looks up in the database, to forward registration information to a Client End by using the registration service provided by the Client End.

The Client End registration service receives the registration information then decodes the registration information and stores them into a corresponding database table.

(2) Archived Resources Monitor and Control Information Uploading Workflow

The PACS Agent Node regularly collects status information of local PACS storage devices or resources, including the physical condition of archiving media, network speed, any machine malfunction, internal hard disk CPU usage rate and so on, creates XML-based structure objects containing the status information of these devices or resources, and uploads the information to Master Node by using the Master Node monitor and control service.

The Master Node monitor and control service receives and decodes the XML-based structure objects, and updates the content of the local Other Resource DB module according to the type of status information. If the service checked and found PACS Agent Node network malfunction or machine malfunction, it then sets the status of this node in the database as non-usable ("N"). If it checked and found damages in the archiving media, it then sets the archiving space status as non-usable ("N"). If a specific device or a node resource was non-usable and the status was marked as "N" in the Other Resource DB module, the Client End would not be allowed to access that node's archived resource (device) when the Client End queried the Master Node to access that device or resource. If the malfunction is recovered, it then sets the corresponding status in the Other Resource DB module as usable ("Y").

(3) Archived Resources Accessing Workflow

When the Client End wants to query the Master Node, it first creates XML-based structure object according to user request, and then invokes the query service provided by the Master Node. The Master Node query service receives the request and decodes the XML-based structure object, find out related image resources information in upper level database based on the query conditions, and looks for whether the image resource indexes and the optimal accessing method to this resource are managed in the lower level local database, or they are managed by the corresponding same level sharing database according to the image series, and finally forms the XML-based responding object including the queried image resource index information and optimal accessing method and return the object to the Client End.

(4) Archived Resources Automatic Backup Workflow

The Master Node Image Backup Allocation Process regularly checks the image distribution situation in the DB module according to image series. If the Process finds that the duplication number of series stored and managed by the Grid PACS Agent Nodes is less than the predetermined number, it may put the series or images UID and the name of PACS Agent Node storing the image series together as a job into a backup task table of Task Management DB module in the Master Node.

The Master Node Backup Allocation Process then gets the job from the backup task table, selects the optimal, sub-optimal backup PACS Agent Node as destination node, creates an XML-based structure object as backup command containing the series UIDs of images needed to be backup and destination node and sends the backup command to the PACS Agent Node which is named as source node and is storing the series of images needed to be backup.

The source node checks the local image archiving situation, creates new backup command which contains the series UIDs of images needed to be backup and addresses of these series, sends new backup command to the destination node.

The destination node checks the local image archiving situation. If the series is not archived in destination node, the destination node sends a start-download command to the source node for the backup, if an error occurs while checking, it sends a check-up-failure message to the source node. The source node invokes the backup transmission service of the Master Node and begins to upload or check failure messages. If the message is failure, the source node still needs to send a backup command to another destination node.

The destination node initiates multi-threads using HTTP (or HTTPS) or FTP (or SSL-FTP) protocol (or other types of communication based on TCP/IP) to download the series of images, and returns the downloaded result to the source node. The source node returns the downloaded result to the Master Node. After receiving it, the Master Node updates the backup task table.

(5) Archived Resources Disaster Recovery Workflow

If the Master Node has received the message about failure of archiving media, network and machine malfunction information sent from a PACS Agent Node, it disable the query and validation services provided by that PACS Agent node to avoid errors when the Client End accesses this PACS Agent node. After that, it initiates the automatic Backup Allocation Process to duplicate the images stored in that malfunction PACS Agent Node in another backup node. The automatic Backup Allocation Process first search the Master Node image registration information to find whether some other PACS Agent Nodes have the image copies stored in the malfunction PACS Agent Node (there are usually, at least, two copies of each image in the Grid PACS system); if there are, the names of source nodes storing the images needed to be backup and the destination nodes being predetermined or configured in Master Node local Other Resource DB module and UIDs of images or series needed to be backup are put together as a job into the backup task table of the Task Management DB module, an XML-based structure objects are created as backup commands based on the job content queued in the task table, and sent to the source nodes to perform the Automatic Backup Workflow as described in Section (4).

When the Master Node has received message about the recovering of archiving media, network and machine malfunction from that malfunction PACS Agent Node, it resumes the stopped services of that PACS Agent Node. In addition, to avoid redundant backups taking up device resources, Master Node checks to see whether the copy number of images or series is more than the predetermined value for that PACS Agent Node and whether they are in the backup task table waiting for backup. If they are, it cancels the backup tasks for those images or series.

(6) Automatic Synchronization of the Same Level Master Node Resource Information In the hierarchical three level structures as showed in FIG. 2, the same level Master Nodes are Master Node 2(A) and 2(B). There are synchronization mechanism to make the same level Master Nodes having same image registration information in their upper level sharing database. The local Task Management DB module not only has the tasks of recording, archiving, deletion, query and validation, but also has the task of same level Master Node synchronization. The local Image Resources DB module and Other Resource DB module of each Master Node is duplicated synchronously or asynchronously at regular intervals to all same Level Resources DB module of other same level Master Nodes, then the results of this synchronization will update the resource registration information of all upper level databases of the same level Master Nodes, and make them identical each other.

(7) Master Node Disaster Recovery Workflow

In a hierarchically-connected three-level structure, the local settings configuration file of each PACS Agent Node may register its connected Master Node (default Master Node), second Master Node (a same level Master Node to the default master node) and the service information provided by the default Master Node and the same level Master Node. This service information may include the Master Node's main machine name, IP address, number of services, service location and service methods. The service method may correspond to the services opened to this PACS Agent Node by the Master Node. When the default Master Node malfunctions, the local PACS Agent Nodes managed by this Master Node may be unable to use the default Master Node's service, and will then automatically use services of another Master Node (the same level master node registered in the configuration file). When the default Master Node recovers from the malfunction, the local PACS Agent Node will automatically switch back to the default Master Node, the resource registration information stored in its upper level sharing database of which is synchronized by the same level Master Node. The system is intended to operate seamlessly without interruption.

(8) The Information Registration Workflow of PACS Agent Node and Client End in Master Node According to system deployment and grid structure, the system administrator may perform PACS Agent Node and Client End information registration through the GUI of Web-Based Grid Management Tool provided by the Master Node: including basic information (host name, IP address, location, network speed) and service information. The service information of the PACS Agent Node refers to the service types, service methods, archiving media and service time. The Client End service information may also include shared resources type, selection of the shared PACS Agent Node and shared time besides the service type and service method.

(9) (Third Party) PACS (or Imaging Equipment) Image Retrieval Workflow of the Grid Middleware After being connected with the third party PACS (or imaging equipment such as CT/MR/Digital X-ray/Ultrasound and so on), the Grid Middleware has three ways to retrieve third party PACS images to index them: actively query the images, actively query and retrieve the images, and passively receive the images.

Actively query the images means that the PACS Agent Node periodically initiates a DICOM Query procedure (as DICOM SCU) and sends the Query request to a third party PACS. The PACS Agent node receives the Query responds, creates manifests containing the UIDs of patient/study/series/(images) of images, then uploads the manifest to the Master Node according to returned query results, the related images of which are registered in Master Node as accessible near line status (images are stored in the connected third party PACS). Active query and retrieve images means that, based on the basis of active images query, the PACS Agent Node (DICOM C-Move SCU) sends the Retrieve request to third party PACS according to queried results, and PACS Agent Node's Image Receiving Procedure receives the third party PACS images, parses the image header information, creates manifests containing the UIDs of patient/study/series/(images) of images, then uploads the manifest to the Master Node, the related images of which are registered in Master Node as online data (images are stored in the PACS Agent Node). Passively receiving images means that the PACS Agent Node Image Receiving Process (as DICOM C-Store SCP) directly receives third party PACS (or imaging equipment)'s images. In addition, after the Image Receiving Process of the PACS Agent Node has received the images, the PACS Agent Node parses the image header information, creates manifests containing the UIDs of patient/study/series/(images) of images, then uploads the manifest to the Master Node, the related images of which are registered in Master Node as online data status (images are stored in the PACS Agent Node).

(10) Request Transmission by Grid Middleware between Client End and Third Party PACS System and Image Routing Workflow After the Master Node has received Client End image query request, it may select the optimal PACS Node to return to the Client End. This workflow is applicable when the PACS Agent Node needs to retrieve images from connected third party PACS and transfer the retrieved images to the Client End. At this time, the third party PACS image's archiving status in the Master Node is usually near-line. The PACS Agent Node will transform or convert the Retrieve request from the Client End into the Retrieve request for the third party PACS, and sent the request to the third party PACS. After receiving third party PACS images, the PACS Agent Node not only transmits these images to the Client End, but also create a manifest containing UIDs of patient/study/series/(images) of received images, and upload the manifest to the Master Node which will change the archiving status of these images from near-line to online.

The invention's PACS Agent Node includes a PACS server function module, and a Basic Grid Agent software operating in the same computer.

The Basic Grid Agent software includes a local resources management module and a monitor and control management module, as well as a Basic Grid Agent Web Service module (or other communication module based on TCP/IP protocol) which is installed in the same computer.

The new image receiving event in the PACS server function module may trigger the Basic Grid Agent Web service (or other types of communication protocol based on TCP/IP) module's Image Registration Process.

The PACS Agent Node may also be the First Grid Agent Node in the hierarchically connected three level grid structures. The image resource registration process may be triggered through lower level Master Node's receiving new image resource registration information or archived resources change information.

In addition, the local machine hardware running status information obtained at regular intervals by the Agent Node may trigger the upload monitor process, and the Agent Node may also perform image validation service for Client End and Master Node in the back end.

According to application needs, through Grid node communication protocol, such as FTP (including SSL-based FTP protocol), HTTP (or other types of communication protocol based on TCP/IP), the PACS Agent Node may transmit or backup imaging documents (images, imaging evidence reports, or other multimedia data) among different PACS Agent Nodes.

The Grid Middleware formed by the PACS Agent Node and the Master Node may actively query and retrieve or passively receive third party PACS(or imaging equipment) images, and may transform or convert the image request between Client End and third party PACS system as well as route the image transmission.

The invention's Master Node may receive, register, process the image resource registration information from the PACS Agent Node, it also may trigger the sharing Client End's uploading process at the same time. The Master node may have a one to many relationship with the PACS Agent Node. Under the hierarchically connected structure, it may have a one to many relationship with the First Grid Agent Node.

The invention's Client End may use RIS, EPR, and PACS workstation function module and perform image resource querying service and validation service. In addition, it may send resource query command to the Master Node according to user request.

The invention's Master Node may receive query requests, process query commands from Client End and select the optimal resource archiving node (best PACS Agent Node for image retrieval) and the optimal service (best image retrieval service) provided to return to the Client End. It may have a one to many relationship with the Client End.

The invention's Master Node may initiate automatic image resource backup process and automatic database synchronization process at regular intervals among same level Master Nodes.

The invention's Master Node has a two level database structure. The upper level database is a resources index level, collecting resources information from lower level database's archives (Image Resource DB module and Other Resource DB module). The local Image Resource DB module and Other Resource DB module of each Master Node has a complete backup in the other same level Master Node's database (Same Level Resource DB module).

The invention's Master Node may provide a GUI of Web-based Grid Management Tool. The system administrator may input the configuration information of PACS Agent Nodes and Client Ends connected with this Master Node. In addition, to provide monitoring information for the purpose of system maintenance and technical support for the Master Node, the Grid management Tool may have a task log, an image archiving distribution monitoring and a nodes archiving partition status management modules.

The invention is a substantial breakthrough compared with existing technologies:

(1) The invented system, through Agent Node<-> Master Node<-> Client End three level structure limitlessly connected in a hierarchical way, utilizes and merges hospital's existing (multiple conforming to DICOM communication standard or given APIs to access to) PACS systems, forming a unified virtual super PACS archived resources pool and enormous user group, realizing medical multimedia (images or other medical records) information distributed storage, virtual central management and utilization.

(2) The invented system, through the Grid Middleware formed by the PACS Agent Node and Master Node, connects the various original (differently structured) PACS storage units or systems with PACS workstations, RIS, HIS as well as EPR and such nodes. By reconnecting together, it forms a new virtual super PACS (Grid PACS). The various PACS storage units or systems and PACS workstations, RIS, HIS as well as RPR cooperatively work under the control of the Grid Middleware formed by the Agent Node and the Master Node. After connecting the same level Master Nodes, the various virtual super PACS can again form a bigger virtual super PACS (a multi-level Grid PACS).

(3) The invented system is characterized by standardization and open structure. It can integrate and connect any PACS system conforming to DICOM communication standard or given APIs to access to the systems, and is not restricted by number of PACSs or geographical location (so long as there is a network connection of certain speed).

(4) The invented system takes full advantage of network features. It optimizes and enhances resource accessing speed, making the user unaware of the distance. The resource synchronization and disaster recovery strategy ensures that the system may operate without intermission, thus showing better system stability and load balance capability.

(5) The invented system, according to the network speed of each node, the machines' usage situation and anticipated performance, will find the optimal backup PACS Agent Node, thus realizing automatic resource backup in different locations.

(6) The invention's Master Node provides a user friendly interactive interface and has the capability to monitor resource distribution, thus making it easier to manage.

(7) The invented system has no side effects to hospital's existing PACS system's operation performance or any effects to its functionality.

DETAILED DESCRIPTION OF THE DRAWINGS

We will use FIG. 1 to FIG. 12 to illustrate a good implementation example and further elaborate on the invention's implementation.

Figure 1:
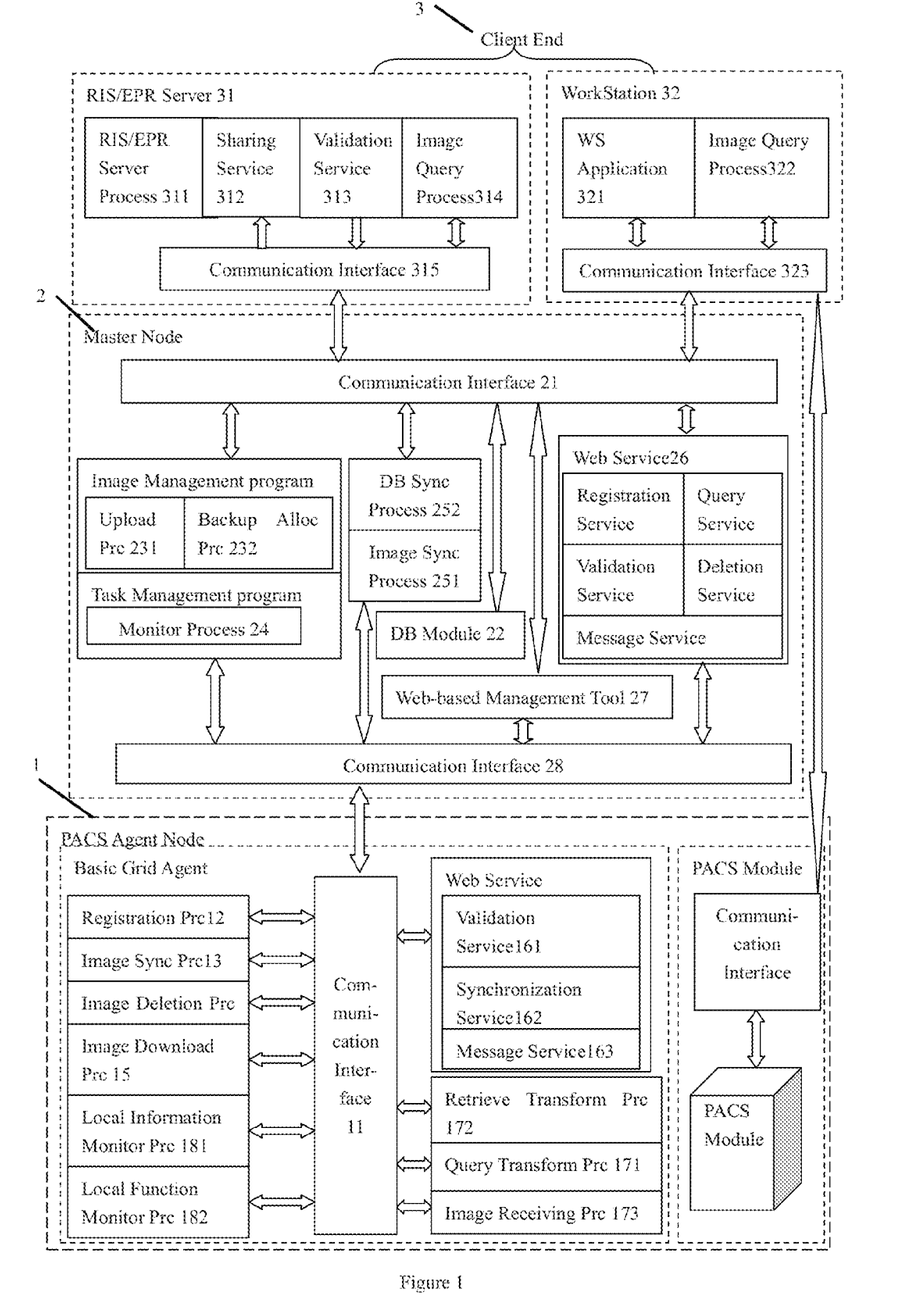
FIG. 1 is about three major components of Master Node, PACS Agent Node and Client End, and their services, processing logic modules as well as database modules of the invention's Cooperative Grid Based Picture Archiving and Communication System.

The invention's Cooperative Grid Based Picture Archiving and Communication System include many PACS Agent Nodes (1), its connected Master Node (2) and various Client Ends (3). The three parts form a PACS Agent Node (1) <->Master Node (2) <->Client End (3) three level working structure. The major service modules, processing logic modules and database modules of key components such as PACS Agent Node, Master Node and Client End are illustrated in FIG. 1). In addition, the PACS Agent Node(1) <->Master Node(2)A and B and a First Grid Agent Node(4) can hierarchically connect with another Master Node(2) and various Client Ends to again form a high level First Grid Agent Node(4)<->Master Node(2)<->Client End(3) three level structure. The information exchange of the various parts is realized by means of Web Service (or other types of communication protocol based on TCP/IP). The system's hierarchical connection structure is as illustrated in FIG. 2, in which the Master Node and the PACS Agent Node will form the Grid Middleware(5) to connect with third party PACS.

The composition of each part is described respectively as below:

First Part: PACS Agent Node (1):

This implementation example includes various PACS Agent Node (1). Each PACS Agent Node is made up of a server with PACS functionality (DICOM C-Store SCP/SCU, DICOM Query/Retrieval SCP/SCU, DICOM WADO SCP, or other kinds of image communication services or APIs) and a Basic Grid Agent software deployed in the same server (see FIG. 1). Besides the original functionality of the PACS server, it also has the capability of local image index uploading with manifest, local image deletion, synchronization with Master Node, local monitoring at fixed intervals and image querying/requesting/transferring/routing with third party PACS. The Basic Grid Agent software and PACS server communicate by using database queue to realize asynchronous communication. The software includes Basic DB module, and Image Download module called by Image Download process (15), Image Registration module called by Image Registration process (12) and Online Image Deletion process (14), Image Validation module called by Image Synchronization process (13), and Monitor module called by Local Information Monitoring process (181), Local Function Monitoring process (182), and validation service (161), Synchronization service (162), Message service (163) provided by Web server. The Basic Grid Agent software and third party PACS (or imaging equipment) communicate by means of DICOM standard or other kinds of image communication services or APIs, including Query Transform process (171), Retrieve Transform process (172) and Image Receiving process (173).

This implementation example's Basic Grid Agent software uses JBuilder as the main development tool. The Web server is Apache Tomcat. The Software installation information is written in the property document and the installation contents vary according to differences in PACS server operating system platform and database, but the Basic Grid Agent software doesn't need to be changed. The property document could be substituted by XML document.

Second Part: Master Node (2):

This implementation example's Master Node is divided into database module (22) which has two level databases and software module. Its functions are: image information registration, registration information sharing with the Client End, task management, same level Master Node synchronization, registration information synchronization with Basic Grid Agent and Client End, automatic image backup allocation and image accessing address optimization. Its software includes Upper Level DB module, Local Resource DB module, Same Level Resource DB module, Task Management module, and Image Validation, Query, Registration, Modification, Backup, Synchronization, Distribution modules, Client End/Agent Node Information Registration/Modification module, Client End/Agent Node Information Query module and Image Management Program, Task Management Program and Synchronization Management Program. It provides query, registration, validation, deletion, monitor, message Web service (26) and Web-based Grid Management Tool (27). The Image Management Program may initiate Upload Process (231) and Image Backup Allocation Process (232). The Task Management Program may initiate Monitor process (24). The synchronization Management Program may initiate Image Synchronization Process (251) between Master Node and PACS Agent Nodes and Database Synchronization Process (252) which synchronizes the lower level database (local Image Resource DB) with remote Master Nodes same level database (Same Level resource DB). The software may use JBuilder or Microsoft (MS).Net as the main development tool. The system platform can be Windows, LINUX, UNIX and the Web server may be Apache Tomcat or MS Internet Information Server (IIS).

Third Part: Various Client Ends (3):

This implementation example's various Client End includes RIS or EPR servers with RIS or EPR functionality and workstations with Image Querying/Receiving and Display modules. Besides the RIS/EPR server process (311), the RIS/EPR server also has Web server providing Image Sharing service (312), Image Validation service (313), Image Query program (314) and a Communication Port (315). The Workstation has WS Application program (321), Image Query program (322) and a communication port (323). The software may use JBuilder or Microsoft(MS).Net as the main development tool. The system platform can be Windows, LINUX, UNIX and the Web server may be Apache Tomcat or MS IIS.

Figure 3:
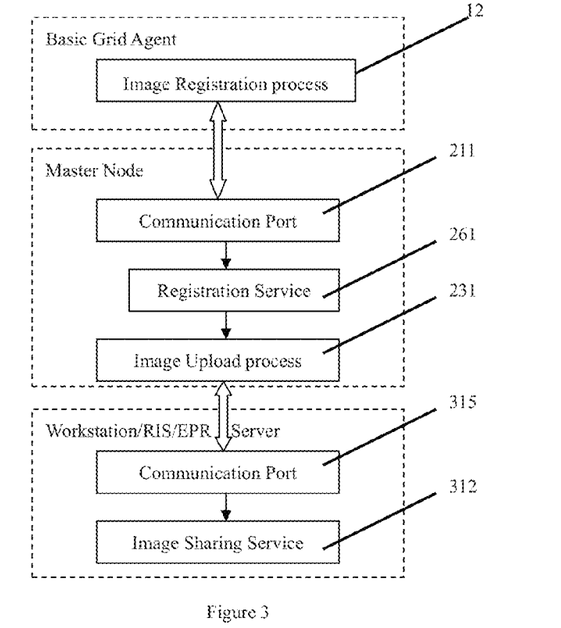
FIG. 3 is an illustration of the manifest (containing the image registration information) uploading and the images sharing process of the invention's Cooperative Grid Based Picture Archiving and Communication System.

This implementation example's PACS Agent Node<->Master Node<->Client End three level structure's main workflow is as follows:

Image Registration:

The workflow is as illustrated in FIG. 3. It includes the Basic Grid Agent Image Registration process (12) in the PACS Agent Node, the Master Node Image Registration service (261), the Master Node Upload process (231) and Client End Image Sharing service (312). After the PACS module has received the images or queried UIDs of patient/study/series/images of images from third party PACS, it stores the files of image series into an upload queue. The Basic Grid Agent's index Registration process (12) then reads this queue, parses the header information of files, creates manifest containing the UIDs of patient/study/series/images, and invokes the Master Node Registration service (261) to upload the manifest to Master Node. The Master Node Registration service (261) receives the manifest, parses the manifest and registers the UIDs of images into the lower level database (local Image Resource DB) therefore updates the image registration in the upper level database of the Master Node, then puts it into an upload queue. The Master Node Upload process (231) reads the queued upload task, invokes RIS or EPR server's Image Sharing service (312). The communication port 211 or 315 uses SOAP RPC methods.

Figure 7:
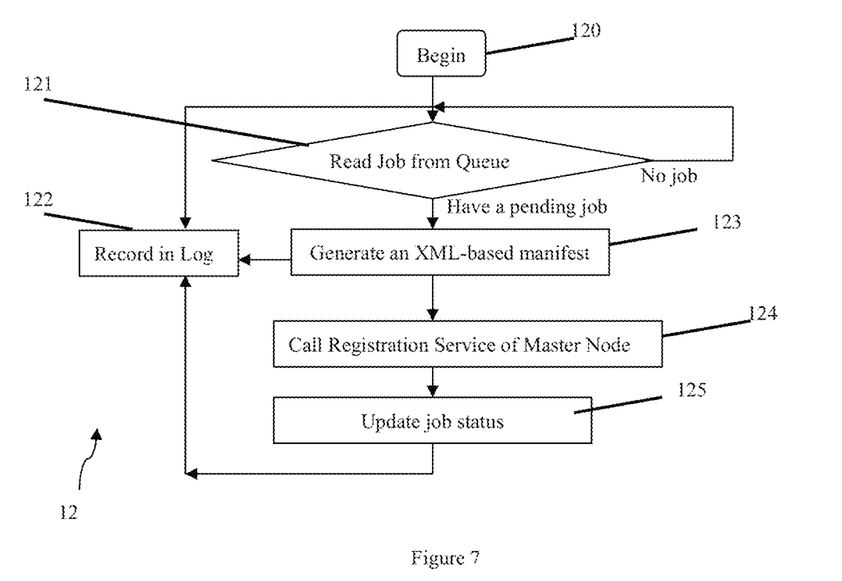
FIG. 7 is an illustration of manifest creating and uploading process of the PACS Agent Node in FIG. 3.

After this implementation example's Basic Grid Agent Registration process (12) is initiated, it checks the upload queue to see whether there exist any new image registration requests. If no requests exist, it then continues the monitoring cycle. If any requests exist it then initiates the sub-thread. The specific flow is as illustrated in FIG. 7. Step 120, process initiated. Step 121, check to see whether there exist any requests in the queue, when none exist it then continues to monitor. Step 122, according to the contents of the request, it parses the header information of the related images, and creates XML-based manifest which contains the UIDs of the images. Step 123, invoke the related registration service method provided by the Master Node to upload the manifest to Master Node. Step 124, use the result (Success or Failure) returned from the Master Node and update the request status of the queue. Step 125, write the log and go to step 121.

Figure 5:
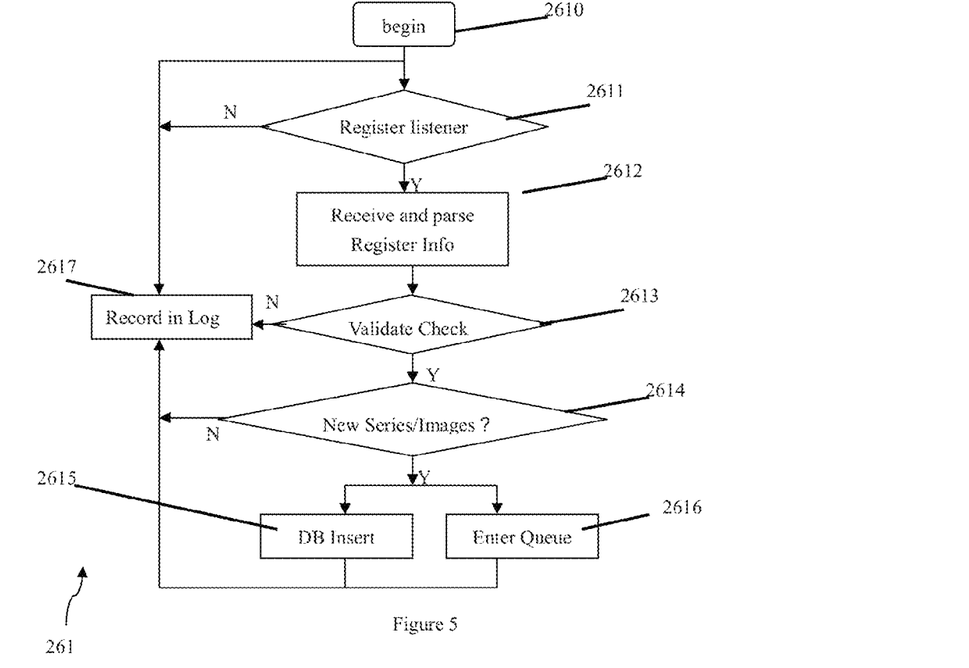
FIG. 5 is an illustration of image registration processing procedure of the Master Node in FIG. 3.

This implementation example's Master Node Image Registration service (261) flow 261 is as illustrated in FIG. 5. Step 2610, service started. Step 2611, check to see whether there are image registration tasks, if none then continue monitoring. Step 2612, receive image registration information contained in a manifest, and parse the information. Step 2613, determine validity of the information, if invalid then go to 2617. Step 2614, determine whether it is an image registration or event message, if it is an event message, perform step 2615, if it is an image registration, perform

2616. Step 2615, enter it into task table. Step 2616, determine whether it is new image registration information, including image archiving status and compression status changes, if it is not new registration, perform step 2617. Step 2615, if it is new registration information, update the image database. Step 2616, the task goes into the upload queue. Step 2617, record the task's processing status, write the log, go to step 2611.

Figure 6:
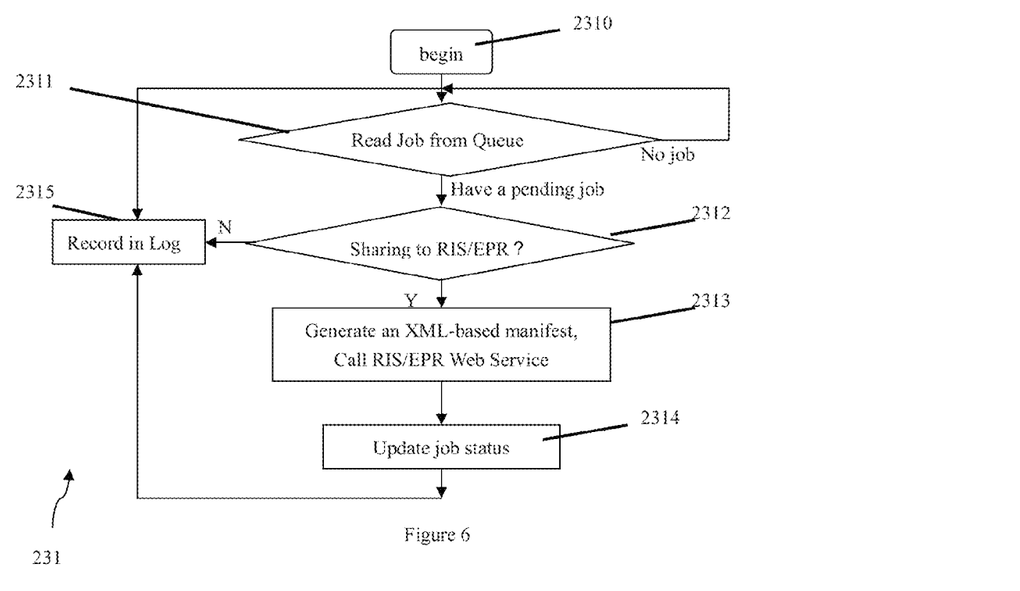
FIG. 6 is an illustration of the processing procedure of image/series registration information uploading to RIS/EPR servers in the Master Node in FIG. 3.

This implementation example's Master Node Upload process (231)'s workflow is as illustrated in FIG. 6, executed consecutively. Step 2310, initiate the process. Step 2311, read the upload queue, when there is no task, continue to monitor the upload queue. Step 2312, determine whether the task of manifest has new image series by comparing with registration database (Local Resource DB) of Master Node. If it contains new series, uploads the registration information of new series to RIS or EPR Client End by Step 2313, if no, go to step 2315. Step 2313, invoke the Web service provided by RIS or EPR Client End. Step 2314, use the returned result from RIS or EPR Client End, and update the queue status. Step 2315, record the task's process status, write logs, go to step 2311.

Figure 4:
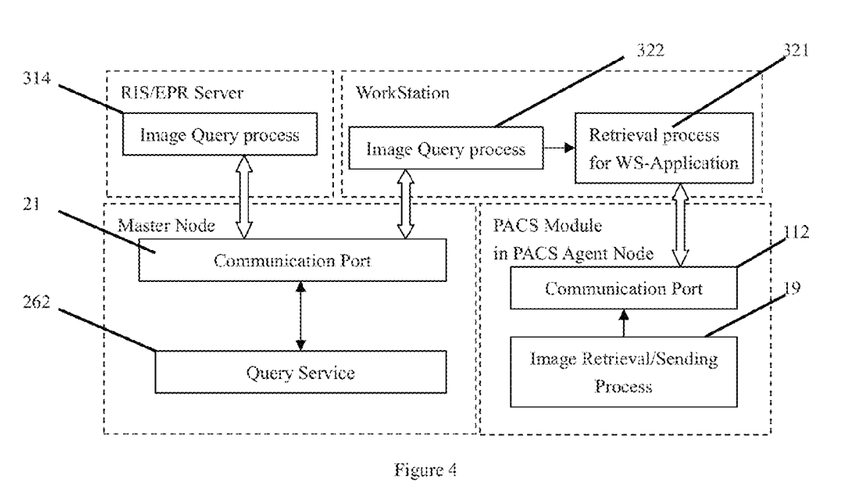
FIG. 4 is an illustration of image query and retrieval process of the invention's Cooperative Grid Based Picture Archiving and Communication System.

Image Query and Retrieval:

The workflow is as illustrated in FIG. 4. Client End Image Query program (314 or 322) invoke the Image Query Service (262) provided by the Master Node. This service calls Image Query module. The Image Query module first search the Upper Level DB module to find whether there are queried images being indexed in the Grid. If there is, find the Master Node which manages the address of the PACS Agent Nodes which really store or manage the images, then may return the optimal accessing PACS node path (best URL or address of PACS Agent Node) and accessing method (e.g., http Get( ) DICOM C-Move, WADO or other accessing interfaces provided by vendors) to the Client End. The Client End Workstation Application program (321), according to the path and method information returned, invokes the PACS Agent Node's PACS function module's corresponding Image Retrieval program (19). The Communication port 21 uses SOAP RPC method, while communication port 112 uses HTTP Get, DICOM C-Move, WADO method according to the preference of Client End's method of retrieving PACS server images.

Figure 8:
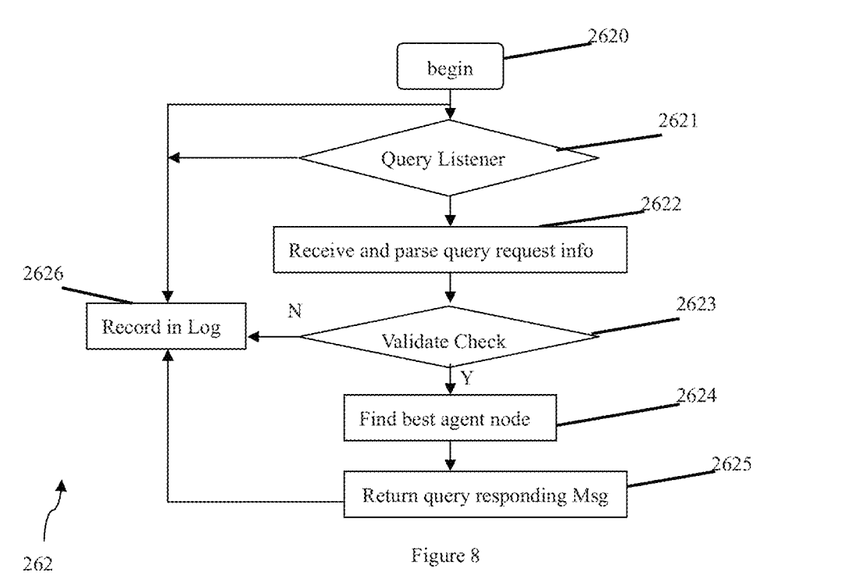
FIG. 8 is an illustration of image query processing procedure of the Master Node in FIG. 4.

This implementation example's Master Node Image Query service (262) receives image query request from the Client End. The specific flow is as illustrated in FIG. 8. Step 2620, start service. Step 2621, monitor and listen to image query request, if none, continue to monitor. Step 2622, receive query request under certain condition information. Step 2623, determine validity of the information, if not valid, return empty information and go to step 2626. Step 2624, find the best accessible PACS Agent Node to the requester node. Step 2625, return the retrieval method and the address or URL information of the best PACS Agent Node to the request node or Client End. Step 2626, record the task's processing status, write logs, go to step 2621.

Image Registration Information Synchronization:

It is to ensure archived image resource uniformity or integrality in the three level structure of the grid. The contents of synchronized checking are:

(a) The RIS or EPR servers and the Master Node's image index information are synchronized. Based on the Master Node, check the RIS or EPR server's image index information. If there are errors in RIS or EPR, correct the image index information of RIS or EPR server to be consistent with Master Node.

(b) The Master Node and the PACS Agent Node's image index information are synchronized. According to the archived image index information in the Basic Grid Agent, check the Master Node's image index information. If there are errors in Master Node, correct the image index information of Master Node to be consistent with PACS Agent Node.

Figure 9:
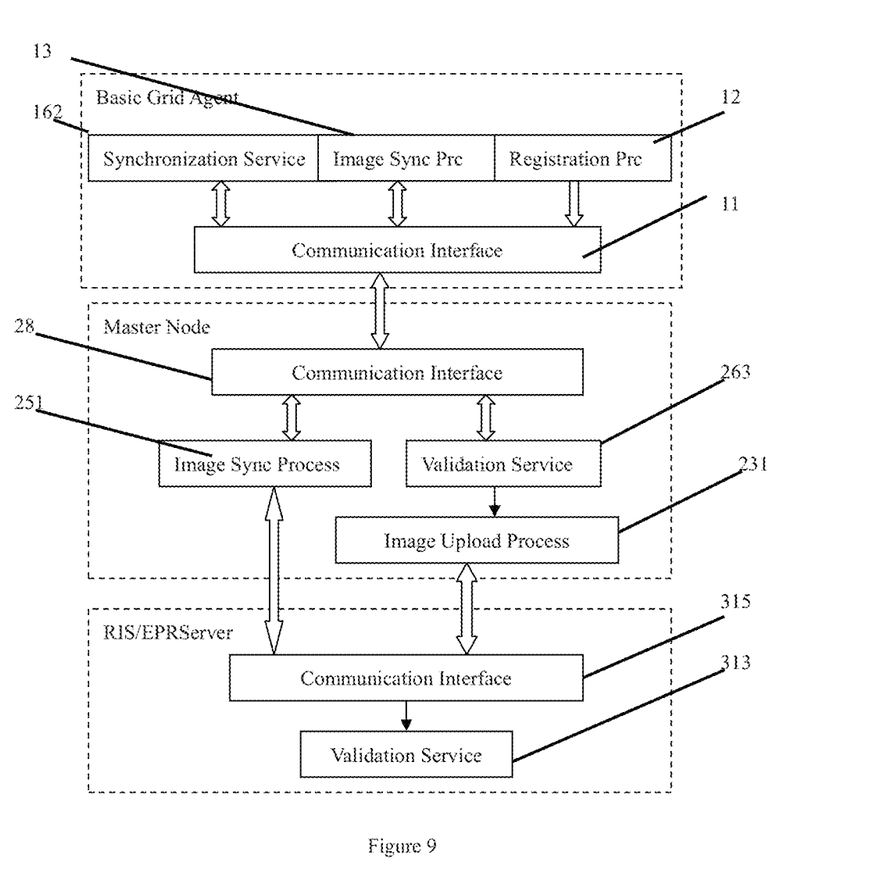
FIG. 9 is an illustration of the image synchronization process between PACS Agent Node and Master Node as well as RIS/EPR servers in the invention's Cooperative Grid Based Picture Archiving and Communication System.

This implementation example's synchronization workflow is as illustrated in FIG. 9:

(1) The Master Node initiates the Image Synchronization process (251). When the Basic Grid Agent synchronization conditions are satisfied such as in a specific period time or receiving a synchronization command from the Master Node, the Image Synchronization process (251) invokes the Synchronization service (162) provided by the Basic Grid Agent. According to the synchronization condition, the Basic Grid Agent initiates Synchronization process (13). The Synchronization process (13) then invokes the Image Validation service (263) in the Master Node to validate the synchronized images. If some images are not registered in the Master Node or the image archiving status has been changed, create a manifest with the image or series UIDs information, add the manifest into an upload queue, then the Upload process (12) get the job of manifest from upload queue and sends the manifest to Master Node through Web-based grid service to update the image index information of the Master Node.

(2) The Master Node initiates the Image Synchronization process (251). When the Client End such as RIS or EPR server synchronization conditions are satisfied such as in a specific period time or receiving a synchronization command from the Master Node, the Image Synchronization process (251) invoke the Image Validation service (313) provided by the Client End. If the image is not shared with the Client End or there is a status change of the image index information in Master Node, the Image Synchronization process (251) create a manifest with the image or series UIDs information, add the manifest into an upload queue, Image Upload process (231) get the job from upload queue and invoke changes the image index information of the RIS or EPR according to the Master Node to make the image index information be consistent between the Client End and Master Node.

This implementation example's Master Node Image Synchronization process (251) regularly checks the resource situation of each Master Node, thus maintaining the system's uniformity and stability. Default Parameters include synchronization time parameter start_sync (it determines synchronization process initiation after how long an interval), sync_longinterval long-term image synchronization interval (it determines all image synchronization for how long an interval), sync_shortinterval image synchronization time interval (it determines image synchronization after how long an interval).

Same Level Master Node Synchronization:

The number of Master Nodes in a grid can be multiple. They can be gridly distributed in multiple places and connected each other through a network with specific arrangement. The image registration information in each Master Node is same to all of Client Ends. Each Master Node directly receives the image registration from the local PACS Agent Nodes registered in it, and mirrored copy the local image registration information to other remote Master Nodes (or called same level Master Node). Each Master Node indirectly receives the image registration mirrored copied from other remote Master Nodes (or called same level Master Node) which come from the remote PACS Agent Nodes. There are two level databases in each Master Node: The upper level database, and lower level database. The upper level database is a resource index layer (RI layer for short) and provides Client Ends all the shared image registration information directly registered from local PACS Agent Nodes and indirectly registered from all other remote PACS Agent Nodes. The lower level database is again divided into local task management database (local Task Management DB), local resource management database (local Image Resource DB and Other Resource DB) and other same level Master Node resource management database (Same Level Resource DB).

The purpose of Same level Master Node synchronization is to guarantee that the image registration information of all the Master Nodes at same level are same each other.

The duplication of this implementation example's lower level local resources database and same level Master Node's resource management database can be realized through Oracle's advanced duplication mechanism synchronously or asynchronously at regular intervals, or through other kinds of multiple database table synchronization methods between different databases provided by database product vendors. The precondition to ensure that the Master Nodes will operate without interruption. This implementation example's Master Node database is OraclelOg, the operating system is Windows Server 2003. But the database can also be Mysql database, SQL Server Database and the operating system can also be LINUX/UNIX.

Figure 10:
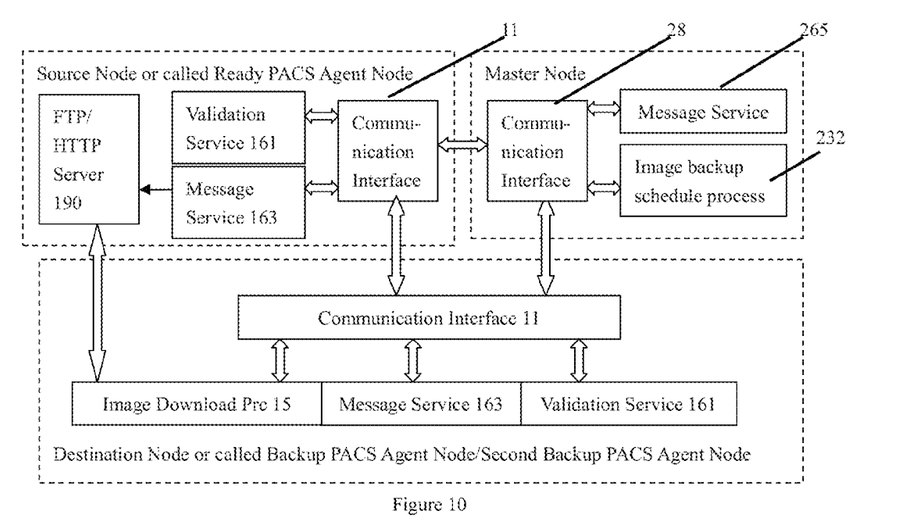
FIG. 10 is an illustration of automatic image backup process between PACS Agent Nodes in the invention's Cooperative Grid Based Picture Archiving and Communication System.

Automatic Image Backup Allocation:

It is one of the adopted measures to ensure safety and reliability of archived images in the grid and uninterrupted system operation. When the number of specific archived images is less than 2, a backup is carried out in a different location for use in disaster recovery. This implementation example's Image Backup Allocation process (232) will automatically use its main thread to complete this task.

This implementation example's automatic backup workflow is as illustrated in FIG. 10: according to the image distribution condition, the Master Node's Image Backup Allocation process (232) calls the Image Distribution module to find out which images are needed for backup, then calls the Client End/Agent Node Information Query module to find out the UIDs of images or series with the parameters describing the image's archiving source node (the PACS Agent Node waiting for the backup), the destination archiving node, second destination archiving node and its image download method (such as FTP, HTTP), finally put the result into the backup task table of Task Management DB module as one message job. The Master Node invokes the Message service (163) of the PACS Agent Node (called source node) waiting for the backup, and sends the backup command with the message to the source node. The Message service (163) of the PACS Agent Node waiting for the backup validates the local images and creates the backup start command with the UIDs of images or series needed to be backup to destination node. The destination PACS Agent Node Image download program (15) initiates multi-threads to carry out the FTP or HTTP (or other types of communication based on TCP/IP protocol) image downloading. If the download is finished or an error occurs, the destination PACS Agent Node invokes the Message service (163) waiting for the backup of source node and then returns the downloaded information. The Message service (163) of the source node decodes the received information and updates the Master Node's task status in a timely fashion.

Web-Based Grid Management Tool:

It mainly monitors the operating situation of the Master Nodes, PACS Agent Nodes, Client Ends and Master Node's logs, including:
(1) The Information registration interfaces of the PACS Agent Nodes connected with the Master Node.
(2) The Client End registration interfaces connected with the Master Node;
(3) The image storage distribution status in the Grid PACS;
(4) The PACS Agent Node image or series archiving statistics information;
(5) The Master Node task log status information.

This implementation example's Grid Middleware formed by PACS Agent Node<->Master Node two level structure has the following main workflow:

Acquiring or Registering Third Party PACS (or imaging equipment) Images

Figure 11:
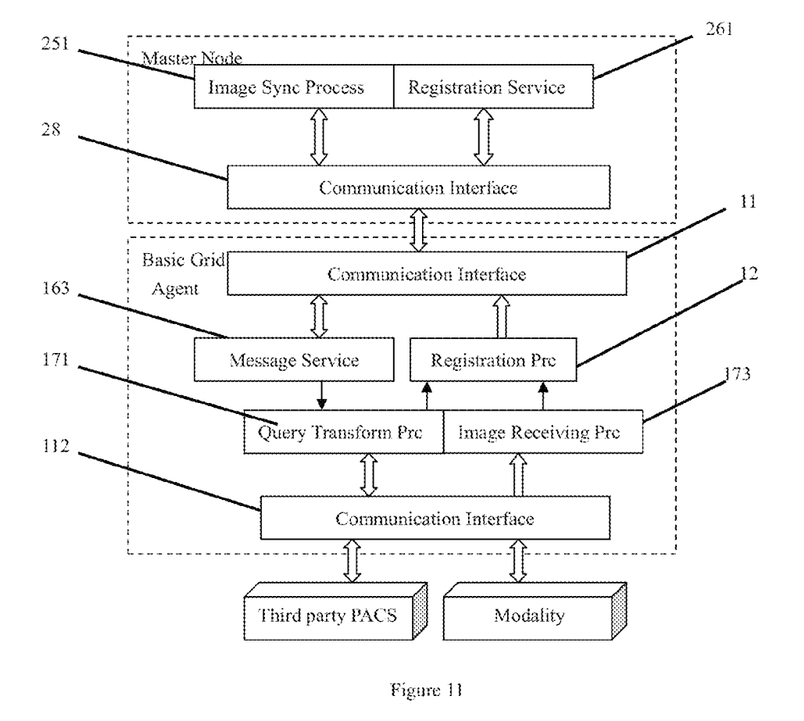
FIG. 11 is a process illustration of the invention's Grid Middleware querying images for image resource registration or retrieving images for image resource registration from third party PACS (or imaging equipment).

This implementation example's Grid Middleware has 3 ways to acquire and register images from third party PACS (or imaging equipment). The three ways are actively query images, actively query and retrieve images and passively receive images or UIDs information of patient/study/series/images. The workflow is as illustrated in FIG. 11. The Master Node Image Synchronization process (251) regularly synchronizes with third party PACS image and invokes Basic Grid Agent Message service (163) to send image synchronization command containing method of retrieval. Using the timestamp as a query condition, the Basic Grid Agent's Query Transform process (171) sends DICOM Query request or other type of query method provided by third PACS vendors to third party PACS and waits for the query result to return. The image retrieval by the Basic Grid Agent according to Master Node has two different ways to execute. One active image query is to add the returned results containing the UIDs of patient/study/series/images into an upload queue and mark the image status as near-line since images are archived in third PACS. Active image retrieval is meant to send DICOM Retrieval requests to third party PACS. The Image Receiving process (173) receives and stores the images in local PACS Agent Node, creates a manifest containing UIDs of patient/study/series/images of these images, then adds the manifest into upload queue and marks the image status as online The Registration process (12) uploads the manifest to Master Node. The Master Node parses the manifest and registers the images with status as online In addition, passively receiving images means that the Basic Grid Agent's Image Receiving process (173) directly receives new images from third party PACS and creates the manifest, then the Registration process (12) uploads it to the Master Node, which marks the images status as online, or Image Receiving process (173) receives the UIDs of new images from third party PACS and creates the manifest then the Registration process (12) uploads it to the Master Node, which marks the images status as near-line. Communication port 112 uses DICOM standard or other kinds of communication methods provided by third party PACS vendors.

Retrieving Third Party PACS Images

Figure 12:
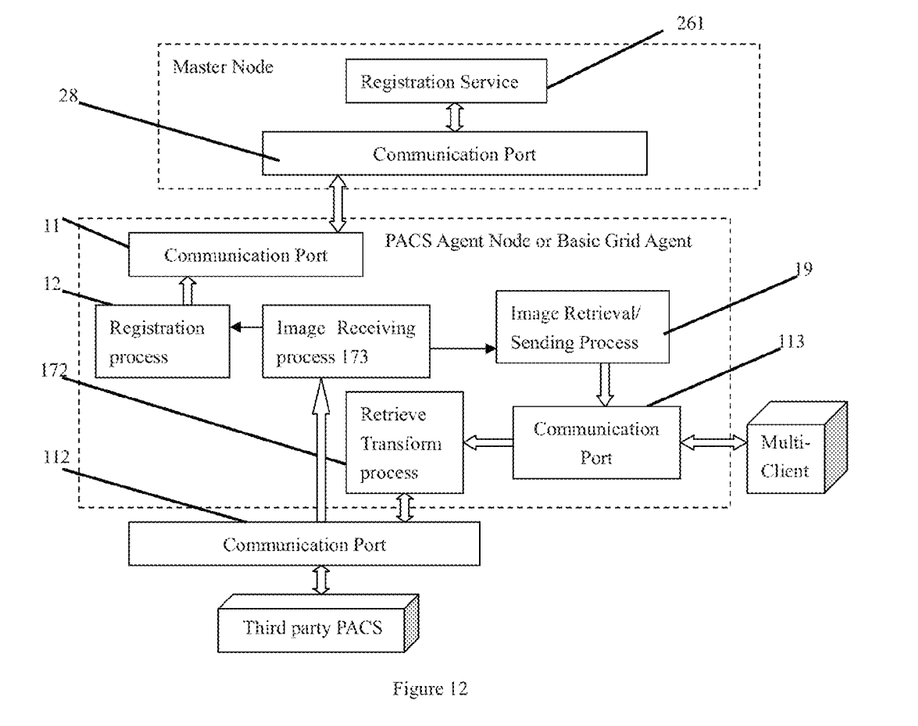
FIG. 12 is an illustration of the invention's Grid Middleware transferring requests between Client End and third party PACS systems, routing the images to the Client End, and registering the images or updating the image storage status from nearline to online in Master Node.

The workflow of this implementation example's Middleware retrieving third party PACS image is as illustrated in FIG. 12. The Client End sends a Retrieval request to the Basic Grid Agent, the Basic Grid Agent's Retrieve Transform process (172) transmits the request to the third party PACS. The Basic Grid Agent's Image Receiving process (173) receives the image from third party PACS. Having received the images, the Basic Grid Agent adds the images into an upload queue according to the image series, sends the manifest with UIDs of the images to Master Node which marks the image status as online The Basic Grid Agent invokes the local PACS module's transfer mechanism to send the images to the Client End at the same time. The Communication port 112 and 113 may use DICOM standard or other kinds of communication methods provided by third party PACS vendors.

What is claimed is:

1. A master node in a cooperative grid based picture archiving and communication system with a three level working structure of agent nodes, client ends and the master node, the master node being responsible for the agent nodes and being connected to each of the agent nodes via a network, each agent node having an associated picture archiving and communications system (PACS), each PACS comprising an image database containing image data including image registration information, the master node comprising a computer processor and master software executable on the computer processor, wherein when the master software is executed by the computer processor, the master node performs the following steps:
   (a) receiving via the network from one of the agent nodes a manifest having image registration information for a plurality of images stored in the image database of the agent node's associated PACS, the image registration information in the manifest including, for each image, information sufficient to retrieve the image from the PACS's image database;
   (b) parsing the manifest to extract the registration information;
   (c) storing the registration information for the plurality of images in a master node database; and
   (d) when the master node receives a query for an image from a client end, searching the master node database to determine whether the image is available in one of the PACSs' image databases, and if the image is available in one of the PACSs' image databases, providing information derived from the registration information for the image received from the agent node associated with that PACS to the client end sufficient to access the image in the PACS's image database.

2. The master node of claim 1, wherein the master node database is synchronized to the databases of the agent nodes.

3. The master node of claim 1, wherein the information provided to the client end sufficient to access the image in the PACS's image database comprises an optimal node path and method for use in accessing the queried image.

4. The master node of claim 3, wherein the cooperative grid based picture archiving and communication system comprises a plurality of master nodes each responsible for a set of agent nodes, and the master node database of each master node is synchronized to the databases of the set of agent nodes for which the master node is responsible.

5. The master node of claim 4, wherein the step of returning an optimal node path and method to the client end comprises determining which master node is responsible for the agent node containing the queried image, and returning the address and access method for that particular agent node.

6. The master node of claim 1, wherein the master node further performs the step of receiving status information from each agent node for which the master node is responsible.

7. The master node of claim 6, wherein the master node further performs the steps of detecting a malfunctioning agent node from the status information, and preventing access to that malfunctioning agent node by client ends.

8. The master node of claim 7, wherein the master node further performs the step of redirecting client ends to alternative agent nodes containing archived images, in the event of a malfunctioning agent node.

9. The master node of claim 8, wherein in the event of the restoration of a previously malfunctioning agent node, the master node further performs the steps of permitting access to the previously malfunctioning agent node by client ends, and cancelling any redundant archiving of images.

10. The master node of claim 1, wherein the master node further performs the steps of:
    (a) searching the master node database for the number of entries of registration data directed to each set of images across all the agent nodes, and
    (b) initiating the distribution of additional copies of those sets of images that are stored on fewer than a predetermined number of agent nodes to backup agent nodes.

11. The master node of claim 1, wherein the cooperative grid based picture archiving and communication system is connected to at least one third party PACS or imaging device via the network, and the master node further performs the steps of:
    (a) receiving a retrieval request from a client end for an image located on the at least one third party PACS or imaging device;
    (b) converting the retrieval request into a transformed retrieval command recognized by the third party PACS; and
    (c) transmitting the transformed retrieval command to the third party PACS.

* * * * *